United States Patent
Almogy et al.

(10) Patent No.: US 7,342,218 B2
(45) Date of Patent: Mar. 11, 2008

(54) METHODS AND SYSTEMS FOR OPTICAL INSPECTION OF SURFACES BASED ON LASER SCREENING

(75) Inventors: Gilad Almogy, Kiriat Ono (IL); Haim Feldman, Nof-Ayalon (IL)

(73) Assignee: Applied Materials, Israel, Ltd., Rehovot (IL)

( * ) Notice: Subject to any disclaimer, the term of this patent is extended or adjusted under 35 U.S.C. 154(b) by 76 days.

(21) Appl. No.: 10/327,534

(22) Filed: Dec. 19, 2002

(65) Prior Publication Data

US 2004/0119001 A1 Jun. 24, 2004

(51) Int. Cl.
*H01J 3/14* (2006.01)
*G01N 27/00* (2006.01)

(52) U.S. Cl. .................... 250/234; 356/237.4
(58) Field of Classification Search ........ 250/234–236, 250/559.42, 559.22; 356/237.2–237.5
See application file for complete search history.

(56) References Cited

U.S. PATENT DOCUMENTS

| | | | | |
|---|---|---|---|---|
| 4,152,723 A | * | 5/1979 | McMahon et al. | 348/126 |
| 4,441,124 A | * | 4/1984 | Heebner et al. | 348/126 |
| 4,968,892 A | * | 11/1990 | McAtee | 250/458.1 |
| 5,359,407 A | | 10/1994 | Suzuki et al. | |
| 5,559,724 A | | 9/1996 | Morrison | |
| 5,639,070 A | * | 6/1997 | Deckard | 264/497 |
| 5,644,141 A | * | 7/1997 | Hooker et al. | 250/559.22 |
| 5,790,620 A | * | 8/1998 | Okazaki et al. | 376/305 |
| 5,963,682 A | | 10/1999 | Dorschner et al. | |
| 6,122,046 A | * | 9/2000 | Almogy | 356/237.2 |
| 6,167,148 A | * | 12/2000 | Calitz et al. | 382/145 |
| 6,236,454 B1 | | 5/2001 | Almogy | |
| 6,381,356 B1 | * | 4/2002 | Murakami et al. | 382/141 |
| 6,549,022 B1 | * | 4/2003 | Cole et al. | 324/752 |
| 6,621,571 B1 | * | 9/2003 | Maeda et al. | 356/237.5 |
| 6,633,376 B1 | * | 10/2003 | Nishida et al. | 356/237.5 |
| 6,636,301 B1 | * | 10/2003 | Kvamme et al. | 356/237.2 |
| 2002/0145042 A1 | | 10/2002 | Knowles et al. | |

OTHER PUBLICATIONS

Born & Wolf, *Principles of Optics*, Seventh Edition, Cambridge University Press, 1999, Chapter 10, pp. 595-607.
Search Report, "International Searching Authority", PCT/US 03/40597, (Dec. 19, 2003).

* cited by examiner

*Primary Examiner*—Thanh X. Luu
(74) *Attorney, Agent, or Firm*—Tarek N. Fahmi

(57) ABSTRACT

A method for imaging and an imaging system, the system includes the steps of: (i) scanning a beam of coherent radiation over a surface along a scan axis; (ii) focusing the beam to a spot on the surface, so that the spot has a predetermined dimension along the scan axis; (iii) spreading the beam laterally while scanning the beam, so that the beam covers an area substantially wider than the predetermined dimension in a direction transverse to the scan axis; and (iii) capturing the radiation scattered from the surface while scanning the beam, so as to form an image of the surface.

7 Claims, 5 Drawing Sheets

METHODS AND SYSTEMS FOR OPTICAL INSPECTION OF SURFACES BASED ON LASER SCREENING

FIELD OF THE INVENTION

The present invention relates generally to laser scanning systems, and specifically to methods and systems for optical inspection of surfaces based on laser scanning.

BACKGROUND OF THE INVENTION

In high-resolution imaging, the use of coherent illumination leads to well-known problems of speckle and loss of resolution. This problem has been studied particularly in the context of microscopy, as described by Born and Wolf in *Principles of Optics* (Seventh Edition, Cambridge University Press, 1999), in Chapter 10, which is incorporated herein by reference. On page 597, the authors note that the resolution of an image taken using coherent illumination is determined by a factor $m=NA_C/NA_O$, wherein $NA_C$ is the numerical aperture of the lens used to focus the illumination onto the image plane (the condenser, in microscopy terms), and $NA_O$ is the numerical aperture of the imaging objective. For optimal image resolution, it is desirable that m be roughly in the range between 1 and 1.5.

SUMMARY OF THE INVENTION

It is an object of some aspects of the present invention to provide an optical imaging system with both high resolution and high throughput.

In laser-based bright-field imaging systems, the laser beam is scanned over a surface being imaged, and the light scattered from the surface is captured by an electronic image sensor. For high throughput, the laser has the advantage of high brightness, and therefore can give high photon flux at the image sensor. High resolution, however, requires that coherence effects be avoided. For this purpose, as explained in the Background of the Invention, it is necessary to focus the laser beam with a numerical aperture at least as great as that of the objective that is used to collect the scattered light. The size of the focal spot of the laser beam is inversely proportional to the numerical aperture. Therefore, when the beam is focused with a high numerical aperture, it is able to scan only very narrow lines, as wide as the focal spot itself. Due to the speed limitations of available scanning devices, the need to cover the surface with a great many of these very narrow scan lines becomes the limiting factor in the throughput of high-resolution imaging systems known in the art.

To overcome this limitation, in embodiments of the present invention, the laser spot is spread laterally on the surface, in a direction transverse to the primary scan axis. In some embodiments, this lateral spread is accomplished by rapid transverse scanning of the laser beam, in a direction perpendicular to the primary scan direction. As a result, the scan lines described by the laser are effectively broadened, without affecting the speed of the primary scan and while maintaining a high numerical aperture in focusing the beam onto the surface. Alternatively, the laser beam may be split into a number of closely-spaced spots, mutually spaced in the transverse direction, and these spots may be scanned together to cover the desired scan area.

In other embodiments, the high numerical aperture, and hence tight focus, of the laser beam is maintained in the direction of the scan axis, but a lower numerical aperture is used in the direction transverse to the scan axis. The focal spot of the laser beam on the surface is therefore broadened in the transverse direction. The scan lines are broadened concomitantly, giving enhanced throughput at the expense of reduced resolution along the transverse direction.

The invention provides a method for imaging, including the following steps: (i) scanning a beam of coherent radiation over a surface along a scan axis; (ii) focusing the beam to a spot on the surface, so that the spot has a predetermined dimension along the scan axis; (iii) spreading the beam laterally while scanning the beam, so that the beam covers an area substantially wider than the predetermined dimension in a direction transverse to the scan axis; and (iv) capturing the radiation scattered from the surface while scanning the beam, so as to form an image of the surface.

The invention provides an imaging apparatus, that includes: (i) a radiation source, which is adapted to generate a beam of coherent radiation; (ii) a scanner, which is adapted to scan the beam over a surface along multiple parallel scan lines having a predetermined spacing therebetween at a rate selected so as to traverse a predetermined linear distance on the surface over the course of a first scan period, each of the scan lines having a scan axis, and which is further adapted, during the first scan period, to scan the beam repetitively in a direction transverse to the scan axis, with a second scan period substantially shorter than the first scan period, so that the beam substantially covers the predetermined spacing between the scan lines; and (iii) optics, which are adapted to focus the beam to a spot on the surface and to collect the radiation that is scattered from the spot, so as to form an image of the surface.

The invention provides an imaging apparatus, including: (i) a radiation source, which is adapted to generate an input beam of coherent radiation; (ii) a beam-dividing element, which is adapted to divide the input beam into a plurality of parallel beams; (iii) a scanner, which is adapted to scan the plurality of parallel beams over a surface along multiple parallel scan lines having a predetermined spacing therebetween, each of the scan lines having a scan axis; and (iv) optics, which are adapted to focus the plurality of parallel beams so as to form on the surface an array of spots, which are disposed along a direction transverse to the scan axis, and to collect the radiation that is scattered from the spots so as to form an image of the surface.

The invention provides an imaging apparatus, that includes: (i) a radiation source, which is adapted to generate an input beam of coherent radiation; and (ii) scanning optics, which are adapted to scan the beam of coherent radiation over a surface along a scan axis and to focus the beam to a spot on the surface, so that the spot has a predetermined dimension along the scan axis, while spreading the beam laterally so that the beam covers an area substantially wider than the predetermined dimension in a direction transverse to the scan axis, the optics being further adapted to capture the radiation scattered from the surface while scanning the beam, so as to form an image of the surface.

The present invention will be more fully understood from the following detailed description of the embodiments thereof, taken together with the drawings in which:

DETAILED DESCRIPTION OF EMBODIMENTS

Figure 1:
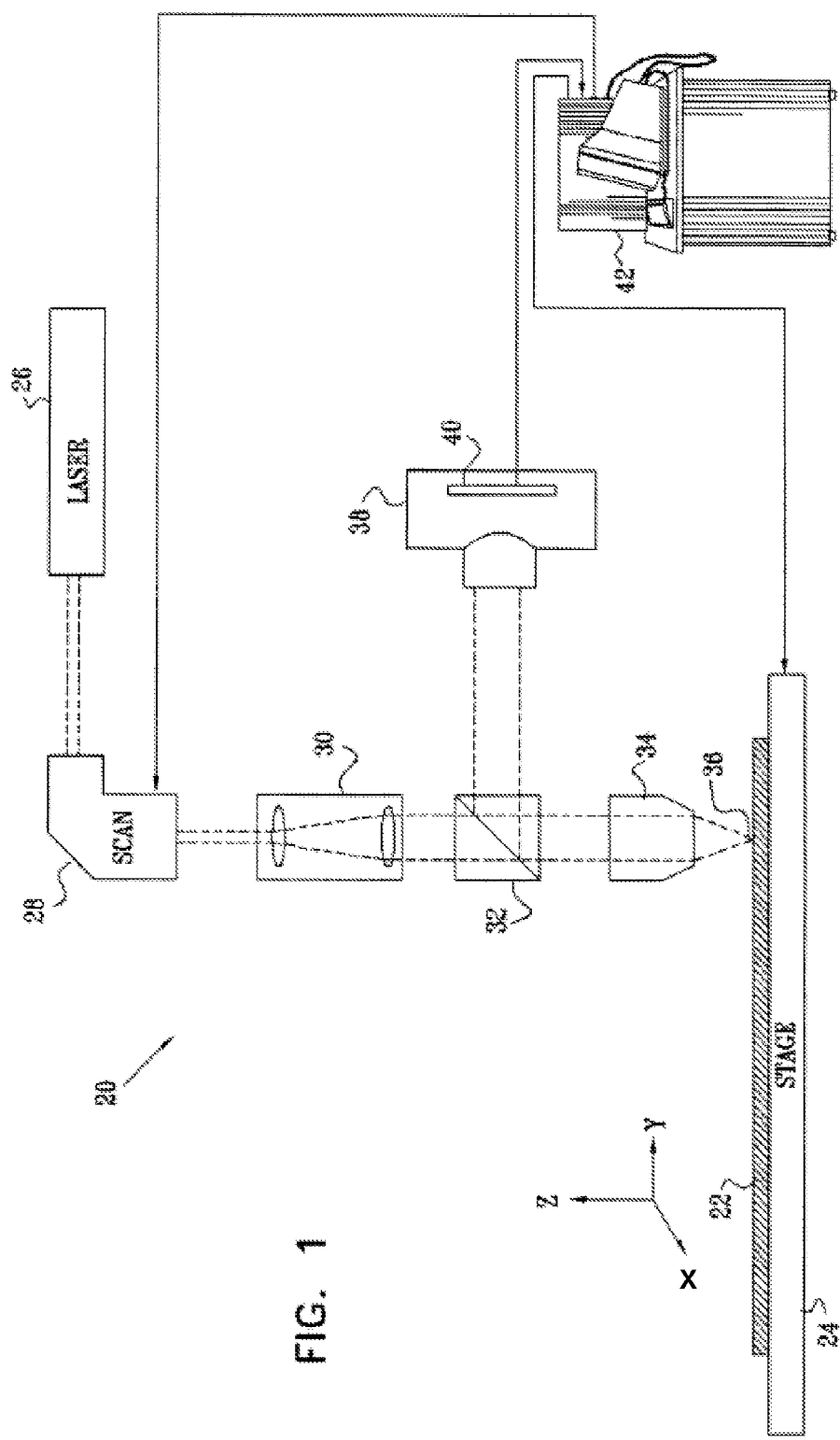
FIG. 1 is a schematic side view of a laser-based bright-field imaging system, in accordance with a embodiment of the present invention.

FIG. 1 is a schematic side view of a system 20 for bright-field imaging of a surface 22, in accordance with a embodiment of the present invention. Typically, surface 22 is the upper surface of a semiconductor wafer, and system 20 is used to observe and detect defects on the surface. The wafer is preferably mounted on a translation stage 24, which positions the wafer for inspection. Alternatively, surface 22 may belong to a substrate or object of substantially any other type that is amenable to bright-field scanning for imaging and/or inspection.

Surface 22 is illuminated by a beam of coherent radiation, preferably from a laser 26. A scanner 28 deflects the laser beam over the surface, along a primary scan axis in the X-direction, i.e., in the direction perpendicular to the page surface in the view shown in FIG. 1. Stage 24 translates surface 22 in steps along the Y-direction, so that the surface is traversed by a series of parallel scan lines. In one embodiment, illustrated below in FIGS. 2 and 3, scanner 28 also adds a rapid transverse deflection to the laser beam, in the Y-direction, in order to effectively broaden the scan lines.

The beam from laser 26 is expanded by a telescope 30, and then passes through a beamsplitter 32 to be focused onto surface 22 by an objective lens 34. The telescope and objective lens together define an effective numerical aperture of the focused laser beam, $NA_C$. Assuming the optics to be diffraction-limited, the laser beam is accordingly focused to a spot 36 on surface 22 whose diameter is approximately $$d = \lambda/NA_C.$$

At a wavelength $\lambda$ of 532 nm, and $NA_C=0.7$, for example, the diameter of spot 36 is therefore about 0.76 µm. The light scattered from spot 36 is collected by objective 34, with a collection numerical aperture $NA_O$. The collected light is reflected by beamsplitter 32 to an electronic imaging camera 38. To minimize coherence effects that reduce the resolution of the image formed by camera 38, system 20 is preferably designed so that $NA_C$ is at least equal to $NA_O$, and is most preferably about 1.5 times $NA_O$, as described in the Background of the Invention. At the same time, for optimal resolution, the value of $NA_O$ is preferably kept as large as possible.

Camera 38 comprises an image sensor 40, preferably a charge-coupled device (CCD) matrix array. Typically, sensor 40 comprises an array of 2048×20 sensors, each approximately 15×15 µm. The sensor includes readout electronics capable of reading out the charge stored in the array elements, preferably at a rate of at least 1 billion pixels/sec. Objective 34 and the optics of camera 38 are preferably designed for a magnification of 60×, so that each image pixel corresponds to an area about 0.25 µm across on surface 22. The focused laser spot, as noted above, covers 3 pixels. An image processor 42 receives and processes the output of sensor 40 to form a high-resolution image of surface 22.

Figure 2:
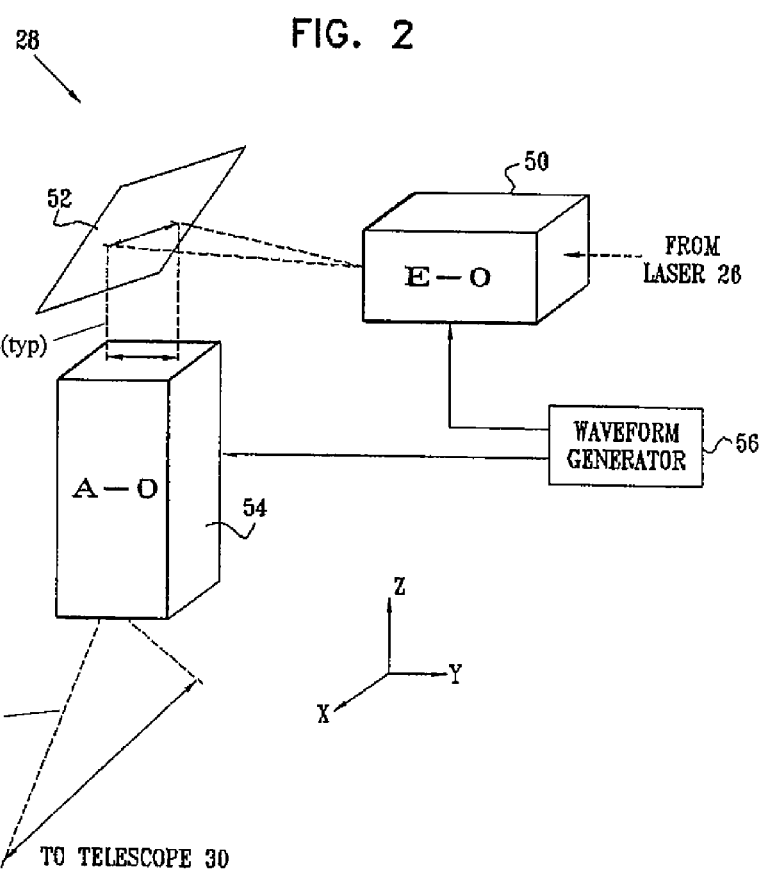
FIG. 2 is a schematic, pictorial view of a dual-axis scanner, in accordance with a embodiment of the present invention.

FIG. 2 is a schematic, pictorial view showing details of scanner 28, in accordance with a embodiment of the present invention. The scanner in this embodiment comprises an electro-optic crystal scanning element 50, followed by an acousto-optic scanning element 54, typically with an intervening turning mirror 52. Acousto-optic element 54 scans the laser beam in the X-direction, i.e., the primary scan direction. The angular extent of the scan is typically approximately 5°, with a typical scan period of 20 µs. This angular scan corresponds to a linear scan traversing about 0.5 mm across surface 22 (depending on the choice of telescope 30 and objective 34). Alternatively, similar scan parameters may be obtained using a high-speed galvanometer mirror or rotating prism, as are known in the art.

Electro-optic element 50 scans the laser beam in the Y-direction. Typically, the scan extent of the electro-optic element is only about 0.0250, corresponding to 5 µm on surface 22, much less than that of the acousto-optic element. On the other hand, the scan period of the electro-optic element is typically only about 10 ns, much shorter than that of scanning elements of other types. A waveform generator 56, preferably under the control of processor 42, generates radio-frequency (RF) waveforms to drive elements 50 and 54 in the desired mutual synchronization.

Figure 3:
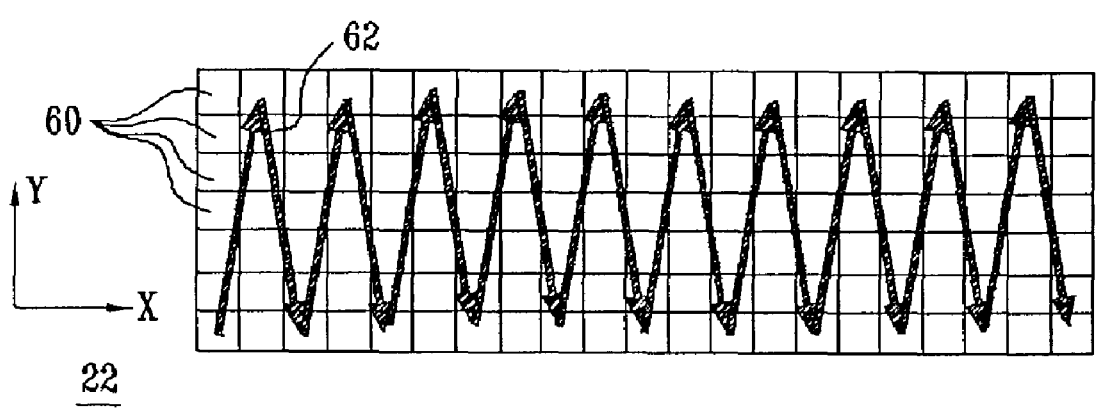
FIG. 3 is a schematic top view of a surface scanned by a laser beam, in accordance with a embodiment of the present invention.

FIG. 3 is a schematic top view of surface 22, showing a scan pattern 62 generated by the scanner shown in FIG. 2, in accordance with a embodiment of the present invention. Pixels 60 of sensor 40 are projected onto surface 22 in this view, as an aid in visualizing the image that is generated by system 20 as a result. As noted above, the size of the focal spot of the laser beam formed on surface 22 is approximately 0.7 µm, while each pixel 60 corresponds to an image area of 15 µm on the surface. Thus, in the absence of transverse scanning element 50, the scan pattern generated on the surface by system 20 would be only about a single pixel in width.

In the example pictured here, however, the transverse deflection of the laser beam expands the scan pattern laterally to about seven pixels in width. Scanning elements 50 and 54 are timed so that element 54 advances the laser beam by the equivalent of two pixels along the scan axis during a single scan period of element 50. Given a scan period of 10 ns for scanning element 50, it can be seen that the laser beam covers surface 22 at a rate of about 7 pixels/ns. Thus, system 20 is able to take advantage of the full readout rate of camera 38, which is typically 1 billion pixels/sec, as described above, substantially without compromising the high numerical aperture used to focus the laser beam onto surface 22. Consequently, both the resolution and throughput of system 20 are optimized.

After completing the scan shown in FIG. 3 over the prescribed scan distance in the X-direction, stage 24 is stepped by a distance roughly equal to the scan width in the Y-direction, i.e., by about seven pixels in the example shown here. The scan pattern is then repeated until the entire region of interest on surface 22 (which may comprise the entire surface) has been imaged.

Whereas FIGS. 2 and 3 shows one specific example of how combined longitudinal and transverse scanning can be accomplished, alternative configurations will be apparent to those skilled in the art. The scanning rates and periods of elements 50 and 54 may be adjusted to accord with different imaging resolution requirements and different sizes and speeds of sensor 40. Moreover, in alternative embodiments of the present invention (not shown in the figures), the longitudinal and transverse scanning functions of scanner 28, as exemplified by FIG. 3, may be accomplished by a single scanning element. For example, acousto-optic element 54 may be driven to deflect the laser beam in both the X- and Y-directions.

Figure 4:
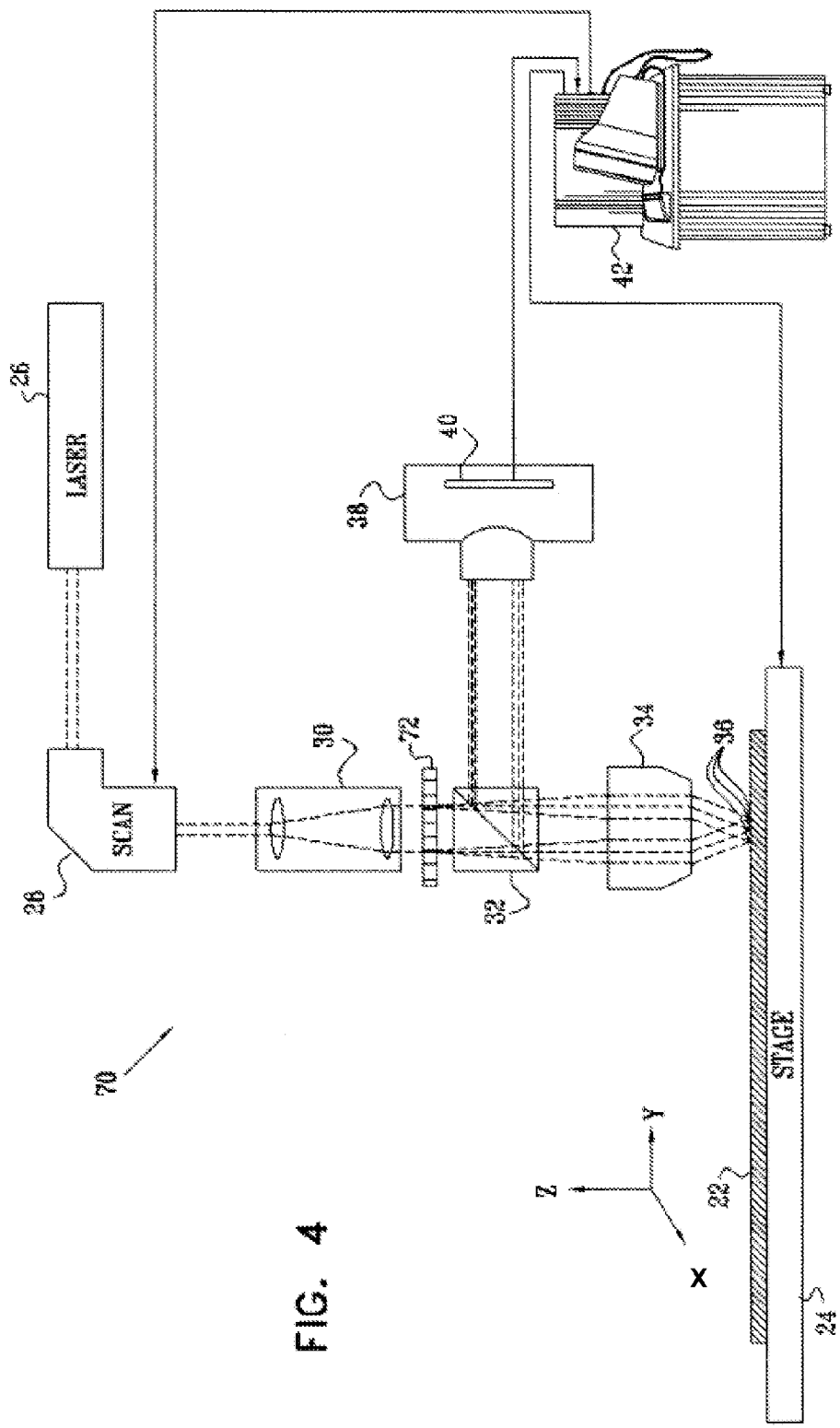
FIG. 4 is a schematic side view of a laser-based bright-field imaging system, in accordance with another embodiment of the present invention.

FIG. 4 is a schematic side view of a system 70 for bright-field imaging of surface 22, in accordance with another embodiment of the present invention. This embodiment is largely similar to that shown in FIG. 1, except for the addition of a beam dividing element 72, which creates an array of spots 36 on the surface, mutually spaced in the Y-direction. Each of the spots preferably has a small diameter and high numerical aperture, as described above. Various methods are known in the art for splitting the laser beam into multiple spots. One example is a Damman grating, which separates an incoming beam into multiple orders of equal power. As another example, an arbitrary beam array may be designed using methods described by Morrison in U.S. Pat. No. 5,559,724, whose disclosure is incorporated herein by reference.

Figure 5:
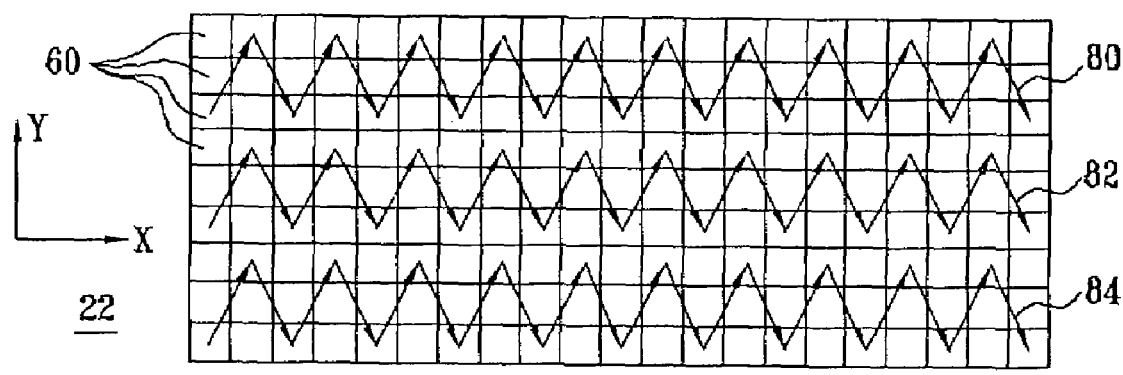
FIG. 5 is a schematic top view of a surface scanned by a laser beam, in accordance with the embodiment of FIG. 4.

FIG. 5 is a schematic top view of surface 22, showing scan patterns 80, 82 and 84 generated in system 70, in accordance with a embodiment of the present invention. In this example, the incident laser beam is split into three equal spots, which are spaced three pixels apart in the Y-direction. The scan patterns of the three spots are similar to pattern 62 (FIG. 3), except that the extent of the lateral scan, in the Y-direction, is substantially reduced. This arrangement reduces the demands on scanner 28 and may enable more rapid overall coverage of surface 22.

In another embodiment of the present invention, not shown in the figures, the laser beam is focused onto the surface with a non-uniform numerical aperture—high NA in the X-direction, preferably equal to or greater than $NA_O$, and lower in the Y-direction. As a consequence of the non-uniform optical configuration, the laser beam forms a focal spot that is elongated in the Y-direction, transverse to the X-direction scan line. Thus, each scan over the surface covers a wide area, as in the embodiment shown in FIG. 3, without the need for additional transverse deflection of the beam by scanning element 50 or other means. The resolution of the image will, of course, be compromised in the Y-direction, but the full resolution afforded in the X-direction is sufficient for some applications.

Although the embodiments described hereinabove use certain particular types of optics and optical configurations, the principles of the present invention may similarly be implemented in other optical systems, using other types of optical components. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An imaging apparatus for producing a plurality of parallel consecutive scan lines on a surface of an article under inspection, comprising:

a radiation source adapted to produce a beam of coherent radiation;

a scanner arrangement adapted to produce an individual one of the scan lines by receiving the beam of coherent radiation and deflecting said beam in two dimensions as projected onto a surface of the article under inspection, a first dimension substantially perpendicular to a translation axis along which the article is translated while undergoing inspection, and a second dimension substantially parallel to the translation axis, wherein a first scan extent of the beam in the first dimension is greater than a second scan extent of the beam in the second dimension and a first scan period of the deflection of the beam in the first dimension is greater than a second scan period of deflection of the beam in the second dimension such that an effective width of the scan line is wider than a width of the beam;

an optical arrangement configured to focus the beam as received from the scanner arrangement onto the surface of the article and to direct scattered radiation from the surface of the article to an imaging sensor having a resolution measured in pixels and being adapted to collect the scattered radiation.

2. The apparatus according to claim 1, wherein the optical arrangement is adapted to focus the beam to a spot having a predetermined dimension, which is substantially smaller than a distance between consecutive ones of the plurality of scan lines as projected onto the surface of the article under inspection.

3. The apparatus according to claim 1, wherein the imaging sensor comprises a camera having a predetermined pixel size and a predetermined readout rate.

4. The apparatus according to claim 1, further comprising an objective, which is configured to collect the scattered radiation with an objective numerical aperture, and to focus the beam with a focusing numerical aperture that is approximately equal to or greater than the objective numerical aperture.

5. The apparatus according to claim 4, wherein the imaging sensor is configured to produce a bright-field image, and wherein the optical arrangement is configured to focus the beam onto the surface of the article under inspection through the objective.

6. The apparatus according to claim 1, wherein the scanner arrangement comprises an acousto-optic element configured to deflect the beam in the first dimension and an electro-optic element configured to deflect the beam in the second dimension.

7. The apparatus according to claim 1, wherein the optical arrangement comprises a beam-dividing element, which is adapted to divide the beam so as to form on the surface of the article under inspection multiple spots, which are disposed along a direction parallel to the translation axis.

* * * * *